United States Patent [19]

Wong

[11] 4,132,788

[45] Jan. 2, 1979

[54] ANTIARTHRITIC POTENTIATION

[75] Inventor: Stewart Wong, Fort Washington, Pa.

[73] Assignee: McNeil Laboratories, Inc., Fort Washington, Pa.

[21] Appl. No.: 862,086

[22] Filed: Dec. 19, 1977

Related U.S. Application Data

[63] Continuation of Ser. No. 683,140, May 4, 1976, abandoned.

[51] Int. Cl.$^2$ .................... A61K 31/40; A61K 31/625
[52] U.S. Cl. ..................................... 424/232; 424/274
[58] Field of Search ................................ 424/274, 232

[56] References Cited

PUBLICATIONS

Physician's Desk Reference (1971), p. 896.
Merck Index, 8th Ed. (1968), pp. 12–13.
J. Pharmacology & Exptl. Therap. 185, 127–138 (1973).
J. Med. Chem., 16 — 172–174 (1973).

*Primary Examiner*—Stanley J. Friedman
*Attorney, Agent, or Firm*—Salvatore R. Conte

[57] ABSTRACT

The anti-inflammatory and antiarthritic properties of 5-aroyl-1-loweralkyl-pyrrole-2-acetic acid derivatives are potentiated by acetaminophen and aspirin.

21 Claims, No Drawings

ANTIARTHRITIC POTENTIATION

This is a continuation of application Ser. No. 683,140 filed May 4, 1976, now abandoned.

BACKGROUND OF THE INVENTION

Within the past few years, a new class of non-hormonal anti-inflammatory agents, namely, certain 5-aroyl-1-loweralkylpyrrole-2-acetic acid derivatives, have been reported. Due to their anti-inflammatory activity, such derivatives are indicated for the inflammation and pain associated with arthritic diseases, e.g., rheumatoid arthritis, osteoarthritis and the like. It has now been found that such derivatives, when combined with two well-known analgesics, acetaminophen and/or aspirin, have greater efficacy in the suppression of inflammation and arthritic degenerations than when administered alone.

DESCRIPTION OF PREFERRED EMBODIMENTS

The 5-aroyl-1-loweralkyl-pyrrole-2-acetic acid derivatives to be employed in this invention are those encompassed within the following structural formula:

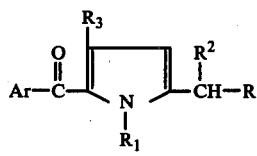

(I)

wherein:
R is a member selected from the group consisting of CN, COOH, COO(loweralkyl), $CONH_2$, CONH(loweralkyl) and CON(loweralkyl)$_2$;
$R_1$ is loweralkyl;
$R_2$ is a member selected from the group consisting of hydrogen and loweralkyl;
$R_3$ is a member selected from the group consisting of hydrogen, loweralkyl, chloro and bromo, provided that when said $R_3$ is chloro or bromo, then said R is COOH; and
Ar is a member selected from the group consisting of phenyl, trifluoromethylphenyl, methylthiophenyl and phenyl substituted with one to three substituents each selected from the group consisting of loweralkyl, loweralkoxy and halo;
and the non-toxic, therapeutically acceptable salts of the foregoing acids, i.e., when R is COOH, such as are obtained from appropriate organic or inorganic bases.

As used herein, "loweralkyl" and "loweralkoxy" may be straight or branch chained saturated hydrocarbons having from 1 to 5 carbon atoms, such as, for example, methyl, ethyl, propyl, isopropyl, butyl, pentyl and the like alkyls, and, respectively, the corresponding alkoxys such as, methoxy, ethoxy, propoxy, isopropoxy, etc.; and "halo" represents chloro, fluoro, bromo and iodo.

The anti-inflammatory compounds of formula (I) are described in U.S. Pat. No. 3,752,826 and in U.S. pat. appln. Ser. No. 591,217 (Filing Date: June 27, 1975; Inventor: John Robert Carson; Title: Halo-Substituted 1-Loweralkyl-5-Aroyl-pyrrole-2-Acetic Acid Compounds).

The preferred compounds of formula (I) for the novel combinations of this invention are those embraced by the formula:

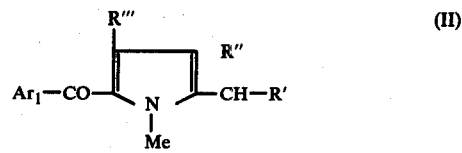

(II)

wherein:
R' is a member selected from the group consisting of COOH and COO(loweralkyl);
R" is a member selected from the group consisting of hydrogen and methyl;
R'" is a member selected from the group consisting of hydrogen, methyl, ethyl, chloro and bromo, provided that when said R'" is chloro or bromo, then said R' is COOH; and
$Ar_1$ is a member selected from the group consisting of phenyl, methylthiophenyl, loweralkylphenyl, loweralkoxyphenyl and halophenyl;
and the alkali metal salts of the foregoing acids, i.e., when R' is COOH.

The more preferred compounds of formula (II) for the novel combinations of this invention are those wherein the substituted phenyls within the term "Ar", are para-substituted. Among the most preferred compounds are 1-methyl-5-p-toluoylpyrrole-2-acetic acid, generically known as "tolmetin", and 1,4-dimethyl-5-p-chlorobenzoyl-pyrrole-2-acetic acid [see J. Med. Chem., 14, 646 (1971); J. Med. Chem., 16, 172 (1973); and J. Pharmcol. Exptl. Ther., 185, 127 (1973)].

When one component of a combination is known to possess a certain pharmacological property and such property is increased many-fold, or known side-effects are concurrently eliminated or reduced, when said component is combined with one or more other drugs, then the net effect of the combination is commonly referred to as "potentiation".

It has now been found that a potentiation of the anti-inflammatory activity possessed by the above-described 5-aroyl-1-loweralkyl-pyrrole-2-acetic acid derivatives is produced by a combination with aspirin or acetaminophen in specified proportions. It has also been found that the latter two drugs also potentiate the anti-arthritic activity of the former derivatives as evidenced by an increased suppression of bone-degenerative changes. Such unique and surprising potentiations are not merely due to the additive effects of the individual components but, rather, are made possible solely and entirely by the action of the combination itself.

It is evident, therefore, that the novel combinations of this invention would find useful applications in alleviating the inflammation, and particularly inflammation, pain and bone degenerative changes associated with arthritic diseases, e.g., rheumatoid arthritis, osteoarthritis and the like.

The efficacy of the novel combination of this invention in inhibiting inflammation and osteogenic degeneration is particularly seen in the adjuvant arthritis test. Although a number of acute anti-phlogistic tests have been devised for the study of inflammation and although inflammation is a common feature of these tests and arthritis, every type of inflammation does not lead to articular (joint) tissue damage that is associated with arthritis. The adjuvant arthritis test, a test in which adjuvant arthritis which results both in inflammation and osteogenic changes is induced by *Mycobacterium butyricum* and in which the effect of test compounds on each effect can be determined, is considered to be most useful for evaluation of compounds which may be suitable for the treatment of rheumatoid arthritis and other arthritic diseases. The test procedure, in which the effect on inflammation is determined by paw volume changes and the effect on osteogenic changes is determined by microscopic observation, is described by Wong et al, in J. Pharmacol. Exp. Ther. 185, 127–138, 1973, and is employed in the present determination of the potentiation of the antiarthritic properties of 5-aroyl-1-loweralkyl-pyrrole-2-acetic acid derivatives by aspirin or acetaminophen.

Briefly, in this procedure, adjuvant arthritis is induced in female Wistar, Lewis rats (Charles River Breeding Laboratories, Inc., Wilmington, Mass.) weighing 160–190 gm by a single subcutaneous injection of 0.75 mg *Mycobacterium butyricum* (Difco) into the left hind paw. The non-injected hind paw remains a normal size for the first seven days. Swelling begins to appear in the non-injected paw of the first rats on Day 8. Using the paw volume determination technique (a technique in which rat paws are dipped in mercury to the hairline and the volume of displacement determined by a modified Van Arman mercury displacement method as described in the aforementioned paper of Wong et al), the time progress curve of volume changes in the non-injected (contralateral) paw is followed. Since it has been found that whenever an animal shows edema $\geq$ 0.25 ml, further increase in the contralateral paw size always follows with swelling developing rapidly during the next two to three days, the 0.25 ml edema is used as criterion of arthritis onset. The mean onset time for 100 rats is found to be 11.6 days with a standard deviation of 1.9 days and the frequency of onset time values distributed normally between Days 8 and 19. Thus, determinations of antiarthritic activity are made in the period Day 11 to Day 28.

It has been found that the progress of adjuvant arthritis can be divided into four phases: Phase I (generally Days 0–10) is the incubation period, Phase II (generally Days 11–18), the time of rapid development of swelling, Phase III (generally Days 19–25), the period of established adjuvant arthritis and Phase IV (generally after 25 Days), the phase of osteogenic changes.

For determination of anti-inflammatory properties two different evaluations are made: (a) the evaluation of paw volume during the Phase II and Phase III periods and, (b) the evaluation of osteogenic (bone) degeneration during the Phase IV period.

For evaluation of paw volume, adjuvant arthritic rats with early but significant signs of arthritis in the contralateral paw are selected on Day 11 and randomly assigned to the various groups of 10 animals in each group. All test animals are dosed daily (per os) with the test compound, preferably as sodium salt, or in saline for 17 days (Days 11 to 27 inclusive). Control animals are dosed with an equivalent volume of saline. The paw volumes of the non-injected paws are determined initially on Day 11 and again on Day 15, 18, 22, 25 and 28. The paw volumes are then compared with normal paw volumes of adjuvant arthritic rats previously determined from a reference curve relating normal paw volume to body weight. The volume of each individual rat which is greater than the normal volume is utilized in the analysis of the data. Values for drug treated animals are expressed as a percent inhibition of the paw volume change relative to the mean value for saline controls. Data is evaluated statistically and $ED_{50}$ values with 95 percent confidence limits are calculated. The method for statistical analysis is described in detail in the aforementioned paper of Wong et al. The term "$ED_{50}$" refers to the dose of drug required to produce 50 percent antagonism of the paw volume changes observed in the saline treated adjuvant arthritis controls. Suppression of paw volume changes reflects anti-inflammatory and antiarthritic activity of a test drug.

For evaluation of bone degenerations, normal and adjuvant arthritic rats are sacrificed under $CO_2$, after the paw volume measurements have been completed on Day 28. The hind legs are removed above the knees and skinned and the soft tissues dissected away with care to avoid injury to bone and articular structures. The leg bones are then immersed in 2 percent potassium hydroxide solution for approximately four to five days until the remaining soft tissues becomes properly macerated and/or transparent, and the bones are fully visible. The leg bones are stained with Alizarin Red (0.01 percent in 2 percent KOH) for eight hours, and then processed through increasing concentrations of glycerol in water (20, 40, 60, 80 and 100 percent) for purposes of clearing the tissues for microscopic observation. The distal end of the tibiae, the tarsals, metatarsals, phalanges, and sesamoids are evaluated under a Stereozoom Microscope (a special type of dissecting microscope, product of Bausch and Lomb).

Osteogenic changes for each bone (in 31 bone categories) in the non-injected hind paw are graded on a scale of from 0 to 10 (increasing numerical value corresponding to increasing severity of bone degeneration). A total bone degeneration score is obtained (maximum score/paw = 310 points) and then expressed as a percent score. The mean percent score (95 percent confidence limits) for saline control groups from 26 experiments (184 animals) is found to be 53.4 (50.9–55.9). Percent score values for drug treated animals are expressed as a percent inhibition relative to the mean for the saline control group. Data is evaluated sastistically and $ED_{50}$ values with 95 percent confidence limits are calculated.

Employing the above described procedures, potentiation of antiarthritic activity of 5-aroyl-1-loweralkyl-pyrrole-2-acetic acid derivatives by acetaminophen and aspirin are determined. The application of the above-described procedure is particularly illustrated with 1-methyl-5-p-toluoyl-pyrrole-2-acetic acid, 1,4-dimethyl-5-p-chlorobenzoyl-pyrrole-2-acetic acid and 4-chloro-5-p-chlorobenzoyl-1-methyl-pyrrole-2-acetic acid. It is to be understood that the compounds illustrated are not for purposes of limiting the invention thereto but only to show the useful properties of compounds within the scope of Formula I. (In the experiments hereinafter described, the 5-aroyl-1-loweralkyl compounds are employed as sodium salts but are calculated and expressed as free acids.)

Potentiation of Antiarthritic Activity of Tolmetin (1-methyl-5-p-toluoyl-pyrrole-2-acetic acid) by Acetaminophen I. Paw Volume Studies Determinations of $ED_{50}$ are made of tolmetin, acetaminophen and a combination of acetaminophen with varying dosages of tolmetin. The $ED_{50}$ for tolmetin on the 28th day, and 95 percent confidence limits (C.L.) are 26.4 (22.3–29.6) mg/kg/day. The $ED_{50}$ for acetaminophen and its 95 percent C.L., evaluated under the same conditions, are 576 (504–698) mg/kg/day. The minimum effective dose (MED*) for acetaminophen is found to be 320 mg/kg/day. The results ($ED_{50}$ values) obtained when acetaminophen at 200 mg/kg/day is combined with tolmetin is seen in Table I.

*Med is the dose of drug which will produce a statistically significant difference ($p < 0.05$) from saline treated controls according to Dunnett's procedure described in Wong et al. For these experiments the mean (± Standard Error) for Dunnett's significant difference (DSD) is 23.8 ± 3.2 percent inhibition.

TABLE I

| Day of Evaluation | $ED_{50}$ Values and 95 Percent C.L. (mg/kg/day) | |
|---|---|---|
| | Tolmetin Only | Tolmetin + Acetaminophen |
| 15 | 42.1 (36.7–47.3) | 11.7 (9.69–12.7) |
| 18 | 40.6 (32.9–48.0) | 6.75 (4.82–7.23) |
| 22 | 32.4 (26.9–37.3) | 7.73 (5.88–8.41) |
| 25 | 29.5 (20.0–40.1) | 2.09 (—) |
| 28 | 26.4 (22.3–29.6) | 1.98 (1.44–2.11) |

The decrease in the $ED_{50}$ for tolmetin to 1.98 (1.44–2.11) mg/kg/day shows a 13.3 fold increase in relative potency for tolmetin indicating potentiation by acetaminophen.

It is immediately obvious that the 95 percent C.L. of the $ED_{50}$ values for the various days evaluated with and without acetaminophen do not overlap and therfore are significantly different.

When various doses of acetaminophen (50, 200 and 800 mg/kg/day) are combined with tolmetin, the $ED_{50}$ values for tolmetin are found to decrease with increasing dose of acetaminophen as seen in Table II.

TABLE II

| Treatment Dose of Tolmetin (mg/kg/day) | Percent Inhibition of Paw Volume ± S.E. Dose of Acetaminophen (mg/kg/day) | | | |
|---|---|---|---|---|
| | 0 | 50 | 200 | 800 |
| 0 | 0 | 0 | 27.2 ± 15.5 | 67.8 ± 5.7 |
| 7.5 | 37.8 ± 8.8 | 34.0 ± 6.9 | 58.9 ± 5.4 | 76.3 ± 3.8 |
| 30.0 | 49.3 ± 9.7 | 50.7 ± 6.4 | 74.0 ± 3.4 | 82.7 ± 4.5 |
| 120.0 | 78.4 ± 3.0 | 75.0 ± 5.5 | 82.4 ± 6.4 | 79.4 ± 5.6 |
| $ED_{50}$ values of Tolmetin | 32 | 28 | 3.3 | 0.6 |

The data is evaluated by analysis of variance (as set forth in Wong et al, supra) for a 4 × 5 factorial complete block design, with days representing the block. Comparison of means are carried out using Dunnett's procedure at the 5 percent special protection level. The $ED_{50}$ values for tolmetin, when combined with acetaminophen at 200 and 800 mg/kg/day, are significantly different from that of tolmetin administered without acetaminophen or tolmetin plus acetaminophen at 50 mg/kg/day.

Regression analysis shows that the decrease in the requirement for tolmetin produced by acetaminophen is linearly related to the logarithmic dose of acetaminophen. The regression coefficient (slope of the dose-response curve) and its 95 percent C.L. are 23.4 (13.6–33.3).

The dose of acetaminophen required to suppress the tolmetin $ED_{50}$ by 50 percent is found to be 35.3 (13.4–81.3) mg/kg/day. Since this dose of acetaminophen when administered alone, as no significant effect in the adjuvant arthritis test, acetaminophen given with tolmetin is potentiating the anti-inflammatory activity of tolmetin.

II. Bone Degeneration Studies

A number of studies have shown tolmetin to be effective against the osteogenic changes which occur in the adjuvant arthritic rat. The results obtained when various doses of acetaminophen are combined with various doses of tolmetin and the $ED_{50}$ values determined, the $ED_{50}$ values of tolmetin are found to decrease with increasing dose of acetaminophen as seen in Table III.

TABLE III

| Treatment Dose of Tolmetin (mg/kg/day) | Percent Inhibition of Bone Degeneration ± S.E. Dose of Acetaminophen (mg/kg/day) | | | |
|---|---|---|---|---|
| | 0 | 50 | 200 | 800 |
| 0 | 0 | 0 | 12.6 ± 6.5 | 32.9 ± 3.4 |
| 7.5 | 18.6 ± 6.9 | 13.6 ± 4.4 | 32.8 ± 4.6 | 39.2 ± 4.0 |
| 30.0 | 26.3 ± 3.7 | 18.1 ± 6.7 | 40.3 ± 3.6 | 69.5 ± 5.7 |
| 120.0 | 51.7 ± 6.4 | 48.5 ± 7.9 | 61.7 ± 3.6 | 76.9 ± 2.9 |
| $ED_{50}$ values (mg/kg/day) | 110.5 | 130 | 41.4 | 12.4 |

When similar data from several experiments showing tolmetin alone to be effective against osteogenic change are pooled and the results analyzed the following values are obtained. The regression coefficient of the dose response curve, for osteogenic change and its 95 percent C.L. are 28.9 (27.6–30.2). The $ED_{50}$ for tolmetin and 95 percent C.L. are 89.7 (82.1–102) mg/kg/day. The $ED_{50}$ for acetaminophen and its 95 percent C.L. are 1673 (1563–2008) mg/kg/day with a regression coefficient and 95 percent C.L. 32.3 (31.0–33.6). When acetaminophen at 200 mg/kg/day is combined with tolmetin, the $ED_{50}$ for tolmetin is decreased to 41.4 (29.8–55.3) mg/kg/day, representing a 2.8 (1.8–4.6) fold increase in the potency of tolmetin against bone degenerative changes. Since the response to acetaminophen alone at 200 mg/kg/day is 12.6 ± 6.5 percent inhibition ± Standard Error and not significantly different from controls (Dunnett's Significant Difference (DSD) = 22.7 percent), the results show that acetaminophen significantly potentiates the anti-arthritic activity of tolmetin.

Potentiation of Antiarthritic Activity of Tolmetin by Aspirin

I. Paw Volume Studies

Using the method previously described, determinations of $ED_{50}$ are made of various dosages of aspirin and various dosages of tolmetin. The results seen in Table IV show that the $ED_{50}$ values for tolmetin are found to decrease with increasing dose of aspirin.

TABLE IV

| Dose of Tolmetin (mg/kg/day) | Percent Inhibition ± S.E. (Day 28) Dose of Aspirin (mg/kg/day) | | | | | |
|---|---|---|---|---|---|---|
| | 0 | 25 | 75 | 100 | 150 | 300 |
| 0 | | 15.2 ± 12.6 | 39.6 ± 3.6 | 28.3 ± 8.2 | 34.2 ± 6.0 | 66.2 ± 6.3 |
| 5.6 | 30.5 ± 5.1 | | 36.7 ± 7.2 | | 46.4 ± 6.8 | 70.3 ± 6.4 |
| 11.1 | 34.5 ± 8.0 | 41.5 ± 5.2 | | 53.9 ± 6.5 | | |
| 16.7 | 58.4 ± 8.1 | | 42.6 ± 5.9 | | 63.1 ± 5.4 | 72.2 ± 6.5 |
| 33.3 | 50.8 ± 8.4 | 41.4 ± 7.9 | | 45.7 ± 5.0 | | |
| 50 | 62.6 ± 2.7 | | 60.4 ± 6.9 | | 61.5 ± 4.3 | 75.1 ± 4.4 |
| 100 | 66.4 ± 3.9 | 75.2 ± 7.7 | | 69.2 ± 4.2 | | |

TABLE IV-continued

| Dose of Tolmetin | Percent Inhibition ± S.E. (Day 28) Dose of Aspirin (mg/kg/day) | | | | | |
|---|---|---|---|---|---|---|
| (mg/kg/day) | 0 | 25 | 75 | 100 | 150 | 300 |
| $ED_{50}$ mg/kg | 32.0 | 29.2 | 23.1 | 13.5 | 6.04 | <0.001 |

When data from several similar experiments are pooled and the results analyzed the following values are obtained. The $ED_{50}$ for aspirin and its 95 percent C.L. are found to be 322(299–545) mg/kg/day. Aspirin alone shows a 16.4 ± 11.4 percent inhibition at 25 mg/kg/day and a 28.3 ± 8.2 percent inhibition at 100 mg/kg/day. Both of these responses are not significantly different from the saline control (DSD = 30.8 percent). When aspirin at 25 mg/kg/day is combined with tolmetin (5.6 to 100 mg/kg/day), the $ED_{50}$ for tolmetin is decreased from 26.4 (22.3–29.6) mg/kg/day to 18.5 (12.3–24.7) mg/kg/day. When aspirin at 100 mg/kg/day is combined with varying doses of tolmetin, the $ED_{50}$ of tolmetin decreases to 8.0 (6.2–9.8).

Analysis of the results indicates that $ED_{50}$ values for tolmetin, when combined with aspirin at 150 and 300 mg/kg/day, are significantly different from that of tolmetin administered without aspirin, or tolmetin plus aspirin at 75 mg/kg/day.

Regression analysis shows that the decrease in the requirement for tolmetin produced by aspirin is linearly related to the logarithmic dose of aspirin. The regression coefficient and its 95 percent C.L. are 25.1 (17.8–32.5).

The dose of aspirin required to suppress the tolmetin $ED_{50}$ by 50 percent is found to be 83.6 (60.5–101) mg/kg/day. This dose of aspirin, when administered alone, has no significant effect in the adjuvant arthritis test. Therefore aspirin given in combination with tolmetin will potentiate the anti-inflammatory activity of tolmetin.

II. Bone Degeneration Studies

The results obtained when various doses of aspirin are combined with various doses of tolmetin, and the $ED_{50}$ values of tolmetin determined, it is found that the $ED_{50}$ values of tolmetin are found to decrease with increasing dose of acetaminophen as seen in Tables V and VI.

TABLE V

| Dose of Tolmetin | Percent Inhibiton ± S. E. Dose of Aspirin (mg/kg/day) | | |
|---|---|---|---|
| (mg/kg/day) | 0 | 25 | 100 |
| 0 | | 20.1 ± 5.2 | 22.9 ± 11.0 |
| 11.1 | 28.7 ± 7.7 | 23.4 ± 2.5 | 39.9 ± 8.9 |
| 33.3 | 33.4 ± 3.9 | 31.7 ± 4.6 | 33.7 ± 7.0 |
| 100 | 54.2 ± 1.9 | 60.2 ± 4.1 | 54.6 ± 3.9 |
| $ED_{50}$ (mg/kg) | 89.7 | 68.1 | 47.6 |

TABLE VI

| Dose of Tolmetin | Percent Inhibition ± S. E. Dose of Aspirin (mg/kg/day) | | | |
|---|---|---|---|---|
| (mg/kg/day) | 0 | 75 | 150 | 300 |
| 0 | | 29.5 ± 5.6 | 22.9 ± 3.1 | 59.9 ± 5.4 |
| 5.6 | 26.6 ± 7.0 | 20.7 ± 3.0 | 25.6 ± 4.7 | 50.4 ± 5.5 |
| 16.7 | 27.5 ± 4.9 | 27.5 ± 4.9 | 42.5 ± 10.9 | 52.4 ± 7.8 |
| 50.0 | 34.9 ± 2.7 | 34.9 ± 2.7 | 43.3 ± 6.6 | 71.0 ± 2.5 |
| $ED_{50}$ (mg/kg) | 89.7 | 54.0 | 35 | 7.2 |

When data from several experiments are pooled and the results analyzed the following values are obtained. The $ED_{50}$ for aspirin and its 95 percent C.L. for suppression of osteogenic changes in adjuvant arthritis has been shown to be 382 (367–464) mg/kg/day with a regression coefficient ± percent C.L. 33.4 (32.1–34.6). When aspirin at 25 mg/kg/day is combined with varying doses of tolmetin, the $ED_{50}$ for tolmetin alone 110 (96.7–139) mg/kg/day is decreased to 68.1 (55.9–105) mg/kg/day. When aspirin at 100 mg/kg/day is combined with varying doses of tolmetin, the $ED_{50}$ is further decreased to 47.6 (15.0–62.6) mg/kg/day. Since the response to aspirin alone at 25 and 100 mg/kg/day are 15.2 ± 12.6 and 28.3 ± 8.2 percent inhibition ± S.E. respectively, and not significantly different from controls (DSD = 30.8%), aspirin has potentiated the antiarthritic activity of tolmetin.

Potentiation of Anti-inflammatory Activity of Other Compounds of Formula I

Using the paw volume technique previously described, the effect of acetaminophen and/or aspirin on other 5-aroyl-1-loweralkyl-pyrrole-2-acetic acid compound are determined.

Table VII shows the results obtained when 1,4-dimethyl-5-p-chlorobenzoyl-pyrrole-2-acetic acid alone, acetaminophen alone and the combinations of the two agents are administered in various doses. The $ED_{50}$ values for each case are indicated

TABLE VII

| Dose of 1,4-Dimethyl-5-p-chlorobenzoyl-pyrrole-2 acetic acid | Percent Inhibition ± S.E. (Day 28) Dose of Acetaminophen | | | |
|---|---|---|---|---|
| (mg/kg/day) | 0 | 100 | 200 | 400 |
| 0 | | 2.7 ± 17.4 | 6.6 ± 11.4 | 31.6 ± 6.1 |
| 0.11 | 27.4 ± 10.1 | 35.3 ± 8.9 | 39.1 ± 12.3 | 61.2 ± 3.2 |
| 0.33 | 45.0 ± 6.0 | 48.3 ± 7.0 | 57.8 ± 2.8 | 58.4 ± 4.3 |
| 1.0 | 68.0 ± 7.8 | 74.9 ± 6.2 | 70.0 ± 8.8 | 84.5 ± 5.3 |
| $ED_{50}$ (mg/kg) | 0.40 | 0.36 | 0.21 | 0.04 |

Table VIII shows the results obtained when 1,4-dimethyl-5-p-chlorobenzoyl-pyrrole-2-acetic acid alone, aspirin alone and the combinations of the two agents are administered in various doses.

TABLE VIII

| Dose of 1,4-Dimethyl-5-p-chlorobenzoyl-pyrrole-2-acetic acid | Percent Inhibition ± S.E. (Day 28) Dose of Aspirin (mg/kg/day) | | | |
|---|---|---|---|---|
| (mg/kg/day) | 0 | 75 | 150 | 300 |
| 0 | | 4.1 ± 14.4 | 33.2 ± 7.6 | 28.9 ± 9.4 |
| 0.125 | 17.5 ± 7.5 | 17.3 ± 3.4 | 23.6 ± 9.0 | 51.0 ± 5.2 |
| 0.5 | 43.8 ± 11.8 | 45.6 ± 12.3 | 48.6 ± 9.4 | 48.9 ± 8.3 |
| 2.0 | 68.2 ± 5.3 | 67.9 ± 6.3 | 73.5 ± 5.5 | 64.3 ± 5.0 |
| $ED_{50}$ (mg/kg) | 0.728 | 0.712 | 0.541 | 0.283 |

Table IX shows the results obtained when 4-chloro-5-p-chlorobenzoyl-1-methyl-pyrrole-2-acetic acid alone, acetaminophen alone and the combination of the two agents are administered in various doses.

TABLE IX

| Dose of 1,4-Dimethyl-5-p-chlorobenzoyl pyrrole-2-acetic acid (mg/kg/day) | Percent Inhibition ± S.E. (Day 28) Dose of Acetaminophen (mg/kg/day) | | | |
|---|---|---|---|---|
| | 0 | 50 | 200 | 800 |
| 0 | | 7.6 ± 6.1 | 29.0 ± 12.8 | 75.3 ± 3.9 |
| 0.02 | 18.6 ± 11.7 | 41.2 ± 11.7 | 48.7 ± 5.4 | 80.5 ± 3.6 |
| 0.06 | 61.3 ± 5.3 | 58.1 ± 9.1 | 75.0 ± 2.3 | 91.1 ± 7.2 |
| 0.18 | 78.9 ± 8.7 | 84.0 ± 5.7 | 87.6 ± 6.1 | 88.2 ± 5.8 |
| $ED_{50}$ (mg/kg) | 0.054 | 0.032 | 0.019 | <0.001 |

The foregoing results illustrate the potentiation of the anti-inflammatory and antiarthritic properties of 5-aroyl-1-loweralkyl-pyrrole-2-acetic acid derivatives of acetaminophen and aspirin. The properties are utilized in the methods and compositions of the present invention.

The process of the present invention, namely, a method of inhibiting inflammation and osteogenic degeneration, comprises orally administering to subjects with inflammation and/or osteogenic degeneration, an inflammation and/or osteogenic degeneration inhibiting amount of a 5-aroyl-1-loweralkyl-pyrrole-2-acetic derivative of Formula I or its pharmaceutically acceptable salt as primary active agent together with a potentiating agent selected from the group consisting of aspirin and acetaminophen. The active agents may be administered with or without carrier in the amounts hereinafter set forth. A preferred method of administration is by the use of the novel compositions in unit dosage form as subsequently described.

The operative ranges of the combination of 5-aroyl-1-loweralkyl-pyrrole-2-acetic acid derivative and acetaminophen or aspirin depends to some extent on whether the potentiating agent is acetaminophen or aspirin. Generally when acetaminophen is the potentiating agent, from about 50 to 800 mg/kg of acetaminophen is employed together with from about 0.001 to 100 mg/kg of the 5-aroyl-1-loweralkyl-pyrrole-2-acetic acid compound, and preferably from 100 to 400 mg/kg of acetaminophen with from 0.01 to 50 mg/kg of the 5-aroyl-1-loweralkyl-pyrrole-2-acetic acid compound. When aspirin is the potentiating agent, from about 50 to 300 mg/kg of aspirin is employed with from 0.001 to 100 mg/kg of the 5-aroyl-1-loweralkyl-2-acetic acid compound, and preferably from 100 to 150 mg/kg of aspirin with from 0.01 to 50 mg/kg of the 5-aroyl-1-loweralkyl-pyrrole-2-acetic acid compound.

One of the most preferred 5-aroyl-1-loweralkyl-pyrrole-2-acetic acid compound for use as antiarthritic agent is tolmetin. Because it is of low toxicity, especially in comparison with structurally unrelated nonhormonal anti-inflammatory agents, it is especially desirable as an antiarthritic agent. With the greater efficacy made possible by its use in combination with acetaminophen or aspirin in accordance with the present invention, its potential as an antiarthritic agent is greatly enhanced. The preferred range when a tolmetin-acetaminophen combination is to be employed is from about 50 to 800 mg/kg of acetaminophen per 1.0 to 100 mg/kg of tolmetin and most preferably from about 100 to 400 mg/kg of acetaminophen per 2.0 to 50 mg/kg of tolmetin. The preferred range when a tolmetin-aspirin combination is to be employed is from about 50 to 300 mg/kg of aspirin per 1.0 to 100 mg/kg of tolmetin, and most preferably from about 100 to 150 mg/kg of aspirin per 2.0 to 50 mg/kg of tolmetin.

The outstanding properties are most effectively utilized by use of the novel pharmaceutical compositions of the present invention. To prepare the pharmaceutical compositions of this invention, a 5-aroyl-1-loweralkyl-pyrrole-2-acetic acid compound and a potentiating agent selected from the group consisting of aspirin and acetaminophen are intimately admixed with a pharmaceutically acceptable carrier suitable for oral administration. By the expression "5-aroyl-1-loweralkyl-pyrrole-2-acetic acid compound" as employed above and in the claims is meant not only the compounds defined by Formulas I and II but the pharmaceutically acceptable salts thereof. In preparing the compositions in oral dosage form, any of the usual pharmaceutical media may be employed, such as for example, water, glycols, oils, alcohols and the like for oral liquid preparations such as suspensions, elixirs and solutions; or solid carriers such as starches, sugars, kaolin, lubricants, binders, disintegrating agents and the like for powders, capsules and tablets. Because of their ease in administration, tablets and capsules represent the most advantageous oral dosage form, in which case solid pharmaceutical carriers are employed. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonfuls, tablespoonfuls and the like, and segregated multiples thereof. A dosage unit generally will contain from about 0.1 to 1000 mg of a 5-aroyl-1-loweralkyl-pyrrole-2-acetic acid compound as primary active ingredients together with from about 150 to 1000 mg of aspirin or from about 150 to 2000 mg of acetaminophen. The preferred dosage unit is from about 0.2 to 500 mg. of a 5-aroyl-1-loweralkyl-pyrrole-2-acetic acid compound together with from about 325 to 500 mg of aspirin or from about 325 to 1000 mg of acetaminophen.

When the 5-aroyl-1-loweralkyl-pyrrole-2-acetic acid compound is preferred tolmetin, the dosage unit may contain from about 2.5 to 1000 mg of tolmetin together with from about 150 to 1000 mg of aspirin or with from about 150 to 2000 mg of acetaminophen. Preferably, the dosage unit contains from 5.0 to 500 mg of tolmetin together with from about 325 to 500 mg of aspirin or with from about 325 to 1000 mg of acetaminophen.

The following examples are given to illustrate the novel compositions and are not to be construed as limiting the invention in spirit or in scope.

EXAMPLE I 1000 hard gelatin capsules, each containing 200 milligrams of 1-methyl-5-p-toluoyl-pyrrole-2-acetic acid as primary active ingredient and 325 milligrams of acetaminophen as potentiating agent are prepared from the following formulation:

| | Grams |
|---|---|
| 1-Methyl-5-p-toluoyl-pyrrole-2-acetic acid | 200 |
| Acetaminophen | 325 |

|  | Grams |
| --- | --- |
| Starch | 250 |
| Lactose | 750 |
| Talc | 250 |
| Calcium stearate | 10 |

A uniform mixture of the ingredients is prepared by blending and filled into two-piece hard gelatin capsules. The capsules are suitable to be used for providing satisfactory inhibition of inflammation upon administration to subjects with articular inflammation.

EXAMPLE II

Gelatin capsules are prepared as described in Example I except that in the formulation, 216 grams of sodium 1-methyl-5-p-toluoyl-pyrrole-2-acetate is employed as the primary active ingredient and 325 grams of aspirin is substituted as the potentiating agent, thus providing capsules each containing 216 milligrams of sodium 1-methyl-5-p-toluoyl-pyrrole-2-acetate and 325 milligrams of aspirin.

EXAMPLE III

Gelatin capsules are prepared as described in Example I except that 4.6 grams of 5-p-chlorobenzoyl-1,4-dimethyl-pyrrole-2-acetic acid is substituted as the primary active agent thus providing capsules each containing 4.6 milligrams of 5-p-chlorobenzoyl-1,4-dimethyl-pyrrole-2-acetic acid and 325 milligrams of acetaminophen.

EXAMPLE IV

Gelatin capsules are prepared as described in Examples I and II except that 5.2 grams of potassium 5-p-chlorobenzoyl-1,4-dimethyl-pyrrole-2-acetate is employed as the primary active agent and 325 grams of aspirin is employed as the potentiating agent providing capsules each containing 5.2 milligrams of potassium 5-p-chlorobenzoyl-1,4-dimethyl-pyrrole-2-acetate and 325 milligrams of aspirin.

EXAMPLE V 1000 compressed tablets, each containing as the primary active ingredient 200 milligrams of 1-methyl-5-p-toluoyl-pyrrole-2-acetic acid and 325 milligrams of acetaminophen as potentiating agent are prepared from the following formulation:

|  | Grams |
| --- | --- |
| 1-Methyl-5-p-toluoyl-pyrrole-2-acetic acid | 200 |
| Acetaminophen | 325 |
| Starch | 750 |
| Dibasic calcium phosphate hydrous | 5000 |
| Calcium stearate | 2.5 |

The finely powered ingredients are mixed well and granulated with 10 percent starch paste. The granulation is dried and compressed into tablets using starch as a disintegrant and calcium stearate as a lubricant.

What is claimed is:

1. An oral pharmaceutical composition in dosage unit form suitable for inhibiting inflammation and osteogenic degeneration comprising per dosage unit:
   (1) from about 0.1 to about 1000 mg of a 5-aroyl-1-loweralkyl-pyrrole-2-acetic acid compound as the primary active agent, said compound being a member selected from the group having the formula:

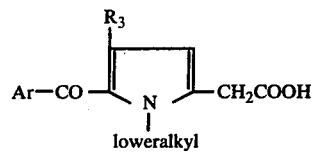

wherein $R_3$ is a member selected from the group consisting of hydrogen, loweralkyl and chloro, and Ar is a member selected from the group consisting of p-loweralkylphenyl and p-halophenyl, and the non-toxic therapeutically acceptable salts thereof; and
   (2) a compound selected from the group consisting of from about 150 to about 2000 mg of acetaminophen and from about 150 to about 1000 mg of aspirin as the potentiating agent;
   wherein said primary and said potentiating agents are in admixture with a pharmaceutically acceptable carrier suitable for oral use.

2. An oral pharmaceutical composition in dosage unit form suitable for inhibiting inflammation and osteogenic degeneration comprising per dosage unit:
   (1) from about 0.1 to about 1000 mg of a 5-aroyl-1-loweralkyl-pyrrole-2-acetic acid compound as the primary active agent, said compound being a member selected from the group having the formula:

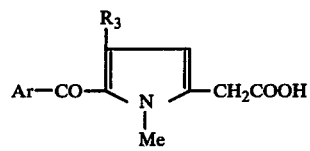

wherein $R_3$ is a member selected from the group consisting of hydrogen, methyl and chloro; and Ar is a member selected from the group consisting of p-methylphenyl and p-chlorophenyl; and the non-toxic therapeutically acceptable salts thereof; and
   (2) a compound selected from the group consisting of from about 150 to about 200 mg of acetaminophen and from about 150 to about 1000 mg of aspirin as the potentiating agent;
   wherein said primary and said potentiating agents are in admixture with a pharmaceutically acceptable carrier suitable for oral use.

3. A composition according to claim 2 in which the dosage unit form is a tablet.

4. A composition according to claim 2 in which the dosage unit form is a capsule.

5. An oral pharmaceutical composition in dosage unit form suitable for inhibiting inflammation and osteogenic degeneration comprising per dosage unit from about 0.1 to about 1000 mg of a member selected from the group consisting of 1-methyl-5-p-toluoyl-pyrrole-2-acetic acid and the alkali metal salts thereof as the primary active agent and a compound selected from the group consisting of from about 150 to about 2000 mg of acetaminophen and from about 150 to about 1000 mg of aspirin as the potentiating agent, wherein said primary and said potentiating agents are in admixture with a pharmaceutically acceptable carrier suitable for oral use.

6. An oral pharmaceutical composition in dosage unit form suitable for inhibiting inflammation and osteogenic degeneration comprising per dosage unit from about 0.1 to about 1000 mg of a member selected from the group consisting of 5-p-chlorobenzoyl-1,4-dimethyl-pyrrole-2-acetic acid and the alkali metal salts thereof as the primary active agent and a compound selected from the group consisting of from about 150 to about 2000 mg of acetaminophen and from about 150 to about 1000 mg of aspirin as the potentiating agent, wherein said primary and said potentiating agents are in admixture with a pharmaceutically acceptable carrier suitable for oral use.

7. An oral pharmaceutical composition in dosage unit form suitable for inhibiting inflammation and osteogenic degeneration comprising per dosage unit from about 0.2 to about 500 mg of a member selected from the group consisting of 1-methyl-5-p-toluoyl-pyrrole-2-acetic acid and the alkali metal salts thereof as the primary active agent and a compound selected from the group consisting of from about 325 to about 1000 mg of acetaminophen and from about 325 to about 500 mg of aspirin as the potentiating agent, wherein said primary and said potentiating agents are in admixture with a pharmaceutically acceptable carrier suitable for oral use.

8. An oral pharmaceutical composition in dosage unit form suitable for inhibiting inflammation and osteogenic degeneration comprising per dosage unit from about 0.2 to about 500 mg of a member selected from the group consisting of 5-p-chlorobenzoyl-1,4-dimethyl-pyrrole-2-acetic acid and the alkali metal salts thereof as the primary active agent and a compound selected from the group consisting of from about 325 to about 1000 mg of acetaminophen and from about 325 to about 500 mg of aspirin as the potentiating agent, wherein said primary and said potentiating agents are in admixture with a pharmaceutically acceptable carrier suitable for oral use.

9. An oral pharmaceutical composition in dosage unit form suitable for inhibiting inflammation and osteogenic degeneration comprising per dosage unit from about 2.5 to about 1000 mg of a member selected from the group consisting of 1-methyl-5-p-toluoyl-pyrrole-2-acetic acid and the alkali metal salts thereof as the primary active agent and from about 150 to about 2000 mg of acetaminophen as the potentiating agent, wherein said primary and said potentiating agents are in admixture with a pharmaceutically acceptable carrier suitable for oral use.

10. An oral pharmaceutical composition in dosage unit form suitable for inhibiting inflammation and osteogenic degeneration comprising per dosage unit from about 2.5 to about 1000 mg of a member selected from the group consisting of 1-methyl-5-p-toluoyl-pyrrole-2-acetic acid and the alkali metal salts thereof as the primary active agent and from about 150 to about 1000 mg of aspirin as the potentiating agent, wherein said primary and said potentiating agents are in admixture with a pharmaceutically acceptable carrier suitable for oral use.

11. An oral pharmaceutical composition in dosage unit form suitable for inhibiting inflammation and osteogenic degeneration comprising per dosage unit from about 5.0 to about 500 mg of a member selected from the group consisting of 1-methyl-5-p-toluoyl-pyrrole-2-acetic acid and the alkali metal salts thereof as the primary active agent and from about 325 to about 1000 mg of acetaminophen as the potentiating agent, wherein said primary and said potentiating agents are in admixture with a pharmaceutically acceptable carrier suitable for oral use.

12. An oral pharmaceutical composition in dosage unit form suitable for inhibiting inflammation and osteogenic degeneration comprising per dosage unit from about 5.0 to about 500 mg of a member selected from the group consisting of 1-methyl-5-p-toluoyl-pyrrole-2-acetic acid and the alkali metal salts thereof as the primary active agent and from about 325 to about 500 mg of aspirin as the potentiating agent, wherein said primary and said potentiating agents are in admixture with a pharmaceutically acceptable carrier suitable for oral use.

13. A method of inhibiting inflammation and osteogenic degeneration which comprises orally administering to an arthritic patient a pharmaceutical composition sufficient to provide from about 0.001 to 100 mg/kg of body weight of a 5-aroyl-1-loweralkylpyrrole-2-acetic acid compounds as the primary inflammation and osteogenic degeneration inhibiting agent, said compound being a member selected from the group having the formula:

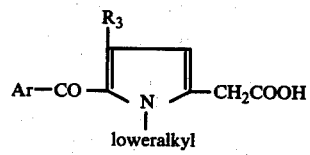

wherein $R_3$ is a member selected from the group consisting of hydrogen, loweralkyl and chloro, and Ar is a member selected from the group consisting of p-loweralkylphenyl and p-halophenyl, and the non-toxic therapeutically acceptable salts thereof; and from about 50 to 800 mg/kg of body weight of acetaminophen or from about 50 to 300 mg/kg of body weight of aspirin as the potentiating agent.

14. A method of inhibiting inflammation and osteogenic degeneration which comprises orally administering to an arthritic patient a pharmaceutical composition sufficient to provide from about 0.001 to 100 mg/kg of body weight of a 5-aroyl-1-loweralkylpyrrole-2-acetic acid compound as the primary inflammation and osteogenic degeneration inhibiting agent, said compound being a member selected from the group having the formula:

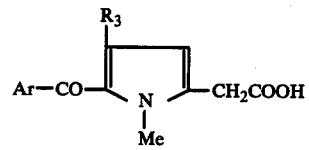

wherein $R_3$ is a member selected from the group consisting of hydrogen, methyl and chloro, and Ar is a member selected from the group consisting of p-methylphenyl and p-chlorophenyl, and the non-toxic therapeutically acceptable salts thereof; and from about 50 to 800 mg/kg of body weight of acetaminophen or from about 50 to 300 mg/kg of body weight of aspirin as the potentiating agent.

15. A method of inhibiting inflammation and osteogenic degeneration which comprises orally administering to an arthritic patient a pharmaceutical composition sufficient to provide from about 0.01 to 50 mg/kg of body weight of a 5-aroyl-1-loweralkylpyrrole-2-acetic acid compound as the primary inflammation and osteogenic degeneration inhibiting agent, said compound being a member selected from the group having the formula:

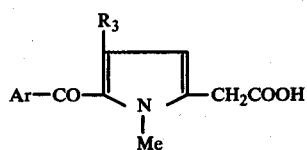

wherein $R_3$ is a member selected from the group consisting of hydrogen, methyl and chloro, and Ar is a member selected from the group consisting of p-methylphenyl and p-chlorophenyl, and the non-toxic therapeutically acceptable salts thereof; and from about 100 to 400 mg/kg of body weight of acetaminophen or from about 100 to 150 mg/kg of body weight of aspirin as the potentiating agent.

16. The method of claim 15 wherein said primary agent is 1-methyl-5-p-toluoyl-pyrrole-2-acetic acid.

17. The method of claim 15 wherein said primary agent is 5-p-chlorobenzoyl-1,4-dimethyl-pyrrole-2-acetic acid.

18. A method of inhibiting inflammation and osteogenic degeneration which comprises orally administering to an arthritic patient a pharmaceutical composition sufficient to provide from about 1.0 to 100 mg/kg of a member selected from the group consisting of 1-methyl-5-p-toluoyl-pyrrole-2-acetic acid and the alkali metal salts thereof as the primary inflammation and osteogenic degeneration inhibiting agent and from about 50 to 800 mg/kg of body weight of acetaminophen as the potentiating agent.

19. A method of inhibiting inflammation and osteogenic degeneration which comprises orally administering to an arthritic patient a pharmaceutical composition sufficient to provide from about 2.0 to 50 mg/kg of a member selected from the group consisting of 1-methyl-5-p-toluoyl-pyrrole-2-acetic acid and the alkali metal salts thereof as the primary inflammation and osteogenic degeneration inhibiting agent and from about 100 to 400 mg/kg of body weight of acetaminophen as the potentiating agent.

20. A method of inhibiting inflammation and osteogenic degeneration which comprises orally administering to an arthritic patient a pharmaceutical composition sufficient to provide from about 1.0 to 100 mg/kg of a member selected from the group consisting of 1-methyl-5-p-toluoyl-pyrrole-2-acetic acid and the alkali metal salts thereof as the primary inflammation and osteogenic degeneration inhibiting agent and from about 50 to 300 mg/kg of body weight of aspirin as the potentiating agent.

21. A method of inhibiting inflammation and osteogenic degeneration which comprises orally administering to an arthritic patient a pharmaceutical composition sufficient to provide from about 2.0 to 50 mg/kg of a member selected from the group consisting of 1-methyl-5-p-toluoyl-pyrrole-2-acetic acid and the alkali metal salts thereof as the primary inflammation and osteogenic degeneration inhibiting agent and from about 100 to 150 mg/kg of body weight of aspirin as the potentiating agent.

* * * * *